United States Patent [19]
Vonk et al.

[11] Patent Number: 6,067,472
[45] Date of Patent: May 23, 2000

[54] PACEMAKER SYSTEM AND METHOD WITH IMPROVED EVOKED RESPONSE AND REPOLARIZATION SIGNAL DETECTION

[75] Inventors: Bernardus F. M. Vonk, Wehl; Geeske van Oort, Nieuwleusen, both of Netherlands

[73] Assignee: Medtronic, Inc., Minneapolis, Minn.

[21] Appl. No.: 09/010,694

[22] Filed: Jan. 22, 1998

Related U.S. Application Data

[63] Continuation-in-part of application No. 08/820,445, Mar. 12, 1997, Pat. No. 5,741,312.

[51] Int. Cl.$^7$ ................................................. A61N 1/362
[52] U.S. Cl. ............................................. 607/28; 607/13
[58] Field of Search ........................... 607/13, 27, 28

[56] References Cited

U.S. PATENT DOCUMENTS

| | | | |
|---|---|---|---|
| 3,835,865 | 9/1974 | Bowers | 128/419 P |
| 4,305,396 | 12/1981 | Wittkampf et al. | 128/419 PG |
| 4,343,312 | 8/1982 | Cals et al. | 128/419 PG |
| 4,373,531 | 2/1983 | Wittkampf et al. | 128/419 PG |
| 4,543,956 | 10/1985 | Herscovici | 607/13 |
| 5,172,690 | 12/1992 | Nappholz et al. | 128/419 PG |
| 5,320,643 | 6/1994 | Roline et al. | 607/28 |
| 5,476,487 | 12/1995 | Sholder | 607/28 |
| 5,697,957 | 12/1997 | Noren et al. | 607/28 |
| 5,718,720 | 2/1998 | Prutchi et al. | 607/28 |

OTHER PUBLICATIONS

U.S. application No. 08/841,095 Peck et al., filed Apr. 29, 1997.

*Primary Examiner*—Kennedy Schaetzle
*Attorney, Agent, or Firm*—Thomas F. Woods; Harold Patton; Michael J. Jaro

[57] ABSTRACT

There is provided a pacemaker system with capture verification and threshold testing, in which the pacemaker adjusts the post-stim pulse portion of a triphasic pulse to minimize polarization, and waits after each change in delivered pace pulses for a stabilization interval, in order to enhance capture verification. The threshold test utilizes a pace pulse pair, comprising a prior search pulse which is varied during the test, and the regular pacing pulse which is above threshold. When delivery of the pulse pairs is initiated, the search pulse is adjusted to optimize polarization, and the pacemaker waits for a predetermined stabilization period of time in order to allow for minimum polarization and to optimize capture detection. The search pulse is increased incrementally in output value toward threshold, and following each such increase the pacemaker waits for a stabilization interval. The pacemaker detects when capture is achieved by the search pulse, thereby providing an indication of threshold. The polarization minimization feature involves scanning the post-stim duration to find the optimal duration. The polarization minimization also enables detection of repolarization signals, and consequent pacemaker functions such as AAIR pacing and suppression of atrial tachycardia.

13 Claims, 6 Drawing Sheets

Fig. 1

_Fig. 2A_

_Fig. 2B_

_Fig. 2C_

FIG. 7

PACEMAKER SYSTEM AND METHOD WITH IMPROVED EVOKED RESPONSE AND REPOLARIZATION SIGNAL DETECTION

REFERENCE TO RELATED APPLICATION

This application is a continuation-in-part of U.S. application Ser. No. 08/820,445, now issued as U.S. Pat. No. 5,741,312 filed Mar. 12, 1997, titled Pacemaker System and Method With Improved Capture Detection and Threshold Search, assigned to the assignee of this application.

FIELD OF THE INVENTION

This invention relates to pacemaker systems and methods and, more particularly, pacemaker systems which provide for capture detection and automatic threshold determination, and for detection of repolarization signals.

BACKGROUND OF THE INVENTION

A chronic problem in the pacemaker art is that of minimizing the output energy of delivered stimulus pulses, either the ventricular pulse (VP) for a single chamber ventricular pacemaker, the atrial pulse (AP) for an atrial pacemaker, or both VP and AP for dual chamber pacemakers. Although battery sources have improved greatly in recent years, so too have capabilities for performing additional functions, such as obtaining and storing diagnostic data, telemetering such stored information or other pacemaker parameter data to an external programmer, etc. These new functions are enabled by dramatic advances in the area of data processing, particularly with the increased use of microprocessors and associated memory. Accordingly, whatever the battery capacity, the pacemaker manufacturer is constantly seeking additional ways to save energy so as to enable performance of additional functions while maintaining effective pacemaker lifetime. Thus, in designing future products it is more and more important to minimize the pulse output energy. This leads to the need for accurate measuring of evoked P and/or R waves, to determine whether or not a pace pulse has been effective in stimulating the heart. The technique of determining how low the output energy can be set is known as threshold searching, by which the threshold amount of energy needed to evoke cardiac response is determined. As is known in the art, once the threshold is determined, the pacing level can be set at some safe incremental level above threshold, to optimize the amount of energy delivered through the pace pulses.

The pacemaker patent literature reveals many different schemes for determining threshold to cardiac pacing. See, for example, U.S. Pat. Nos. 3,835,865; 4,305,396; 5,320,643; and 5,476,487. Most threshold searching arrangements rely on accurate sensing of the evoked response, i.e., determining whether the delivered pace pulse "captures" or evokes a cardiac response. However, a major problem has been to detect evoked potentials when they are superimposed on the polarization voltage which is generated at the electrode-tissue interface. Minimization of such polarization at the electrode where the pulse is delivered, and which follows a delivered pace pulse, is essential in measuring the evoked potential, or evoked response. If a large degree of polarization exists, it is difficult to detect an evoked response at the electrode. See U.S. Pat. No. 4,343,312, which provides an output circuit for delivering a triphasic pace pulse designed to minimize polarization and better enable detection of capture or no capture, as well as enabling detection of evoked T-waves. In such a triphasic pulse, pulses of opposite polarity are added both before and after the stimulus pulse, to counteract the buildup of charge at the electrode-tissue interface which would otherwise result from the stimulus pulse.

The present invention is based on the observation that reliable detection of evoked responses, as well as repolarization signals from the ventricle or atrium, requires a stable polarization environment. Thus, reliable capture detection can take place only when polarization has been minimized and stabilized, which condition should be achieved to the fullest possible extent before proceeding with threshold testing. It is accordingly an object of this invention to provide a system and method for capture detection and threshold determination, as well as for repolarization signal detection, which includes minimization and stabilization of polarization.

SUMMARY OF THE INVENTION

There is provided a pacemaker system and method which incorporates an improved technique for optimizing polarization caused by a delivered pace pulse, enabling improved detection of atrial or ventricular evoked responses and repolarization signals. In a preferred embodiment, the system of this invention provides for determining threshold to a delivered pace pulse, either VP or AP, the threshold determination being carried out after optimizing polarization caused by delivery of pace pulses. The pacing pulses are preferably triphasic, and have a positive pre-stimulus portion; a negative stimulus portion; and a positive post-stimulus portion. The polarization optimization routine involves adjusting the duration of the post-stimulus portion until the polarization level after delivery of a pacing pulse is a positive value, and within a predetermined range, e.g., 0.5 to 1.0 mV. When the polarization following delivered pacing pulses, or stimulus pulses, is stabilized within this range, the evoked response can be reliably detected by looking for a negative going signal within a time window following the pacing pulse.

Upon initiating a threshold search, the pacemaker utilizes pairs of separate stimulus pulses, spaced 50–100 ms from each other. A second, or search pulse is generated 50–100 ms before the regular pulse, initially at a relatively small output which is below threshold. The search pulse is also adjusted for minimal polarization, preferably using the adjustment criteria adopted for the regular pace pulses. In order to provide stabilization, the pulse pairs are delivered at constant output levels for a predetermined stabilization period, e.g., 1–20 stabilization pulses. After this, capture is determined by first looking for an evoked response following the relatively low level search pulse, and then following the higher level regular pulse; optionally the time from delivery of the second pulse to detection of the T-wave can also be used to verify whether the search pulse or the regular pace pulse evoked capture. If capture is not found, the search pulse is adjusted to a new and higher value, and again the test waits for a number of stabilization pulses before looking for an evoked response. The steps of increasing the search pulse toward threshold and waiting a predetermined stabilization period, and only then looking for capture, are repeated until it is found that the search pulse has captured the heart, thereby indicating threshold. After this, the regular pace pulse is adjusted as a function of the determined threshold.

The polarization minimization routine of this invention also makes possible reliable detection of repolarization signals, in both the ventricle (T-waves) and atrium. With detection of atrial repolarization signals, AAIR mode pacing and other pacing or anti-tachycardia treatment functions can be carried out.

DESCRIPTION OF THE PREFERRED EMBODIMENTS

Figure 1:
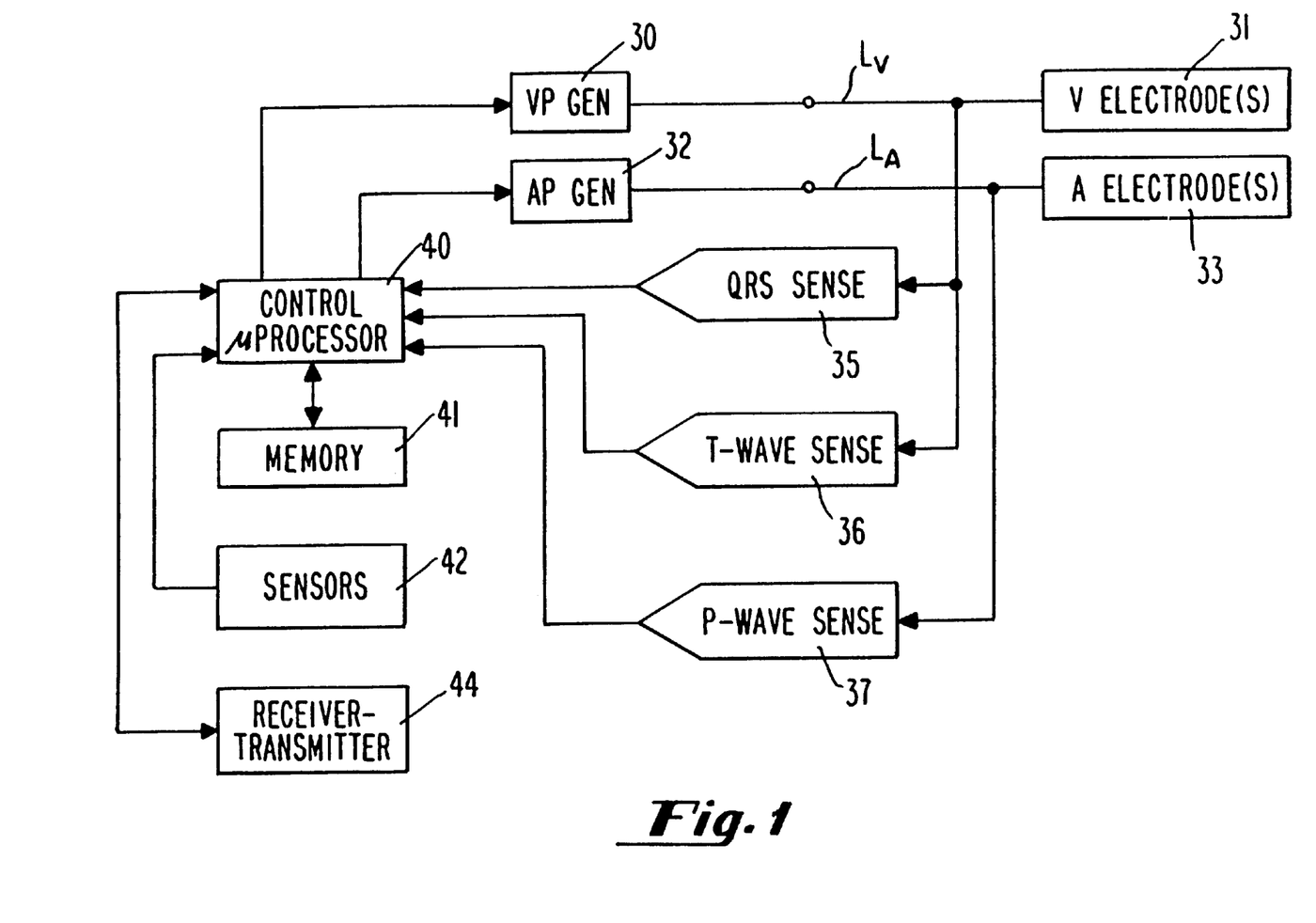
FIG. 1 is a block diagram showing the primary elements of a pacemaker system in accordance with this invention, having incorporated in it a routine for capture detection and threshold search.

Referring now to FIG. 1, there is shown a block diagram of an illustrative pacemaker system for use in the practice of this invention. The block diagram of FIG. 1 shows the primary functional components of a pacemaker, which components and their interconnections are well known in the pacemaker art. A VP generator 30 produces ventricular pace pulses, including pulse pairs as used in this invention, under control of control block 40. The output of generator 30 is connected through a pacing lead $L_V$ to a ventricular electrode or electrodes indicated at 31, for pacing of the patient's ventricle. The electrode or electrodes 31 also sense signals in the patient's ventricle, natural and evoked. Signals sensed at electrodes 31 are connected to a QRS sense amplifier circuit 35, as well as to a T-wave sense amplifier 36. By a technique well known in the art, amplifier 35 is enabled for a window corresponding to the expected arrival of the QRS, under control of circuit 40; similarly the T-wave amplifier is enabled for a window of time around the expected T-wave, likewise under the control of circuit 40. Thus, ventricular senses (VS) and T-waves are detected and inputted into control 40, for use by the pacemaker. For a dual chamber pacemaker, there is also an atrial pulse generator 32, which delivers atrial pace pulses under control of control circuit 40. These pulses are connected through an atrial lead $L_A$ to atrial electrode or electrodes designated at 33. Natural P-waves, or evoked atrial responses, are sensed by the atrial electrodes 33, and connected to P-wave sense amplifier 37, the output of which is connected back to control block 40. Sense amplifier 37 may also switchably be enabled for a window of time corresponding to the expected arrival of the P-wave.

Control block 40 performs the various logic and processing functions of a modern pacemaker, and suitably comprises a microprocessor. The microprocessor circuit itself contains some memory, and there may be additional memory, RAM/ROM, as indicated at block 41. The allocation of hardware and software to the structure and control block 40 is a matter of design choice, and not important to the scope of this invention. Also shown are sensors 42, for determining one or more parameters from which rate responsive control can be achieved, again in a known fashion. Block 44 illustrates a receiver-transmitter for communicating with an external programmer by telemetry, in a known fashion. Thus, program instructions from an external transmitter are received at 44 and coupled into control block 40; likewise data collected by the pacemaker concerning pacemaker operating variables and/or diagnostic data may be downloaded through unit 44 to the external programmer, in a known manner.

Figure 2A:
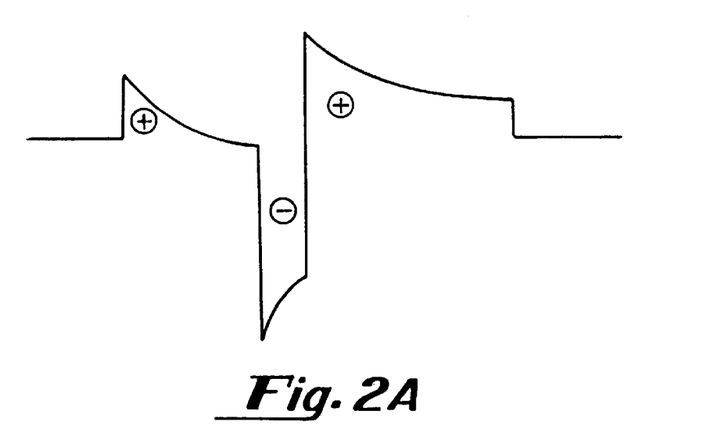
FIG. 2A is a diagram of a triphasic pace pulse designed to minimize polarization.

Referring now to FIG. 2A, there is shown a representative triphasic pace pulse designed to minimize polarization produced by delivery of a pace pulse through an implanted electrode. The triphasic pulse comprises a first positive going portion, a larger negative going portion which is designed to evoke the cardiac response, and a follow-up positive going portion. The parameters, i.e., magnitude and duration, of the respective portions of the triphasic pulse are adjusted to determine the combination which optimally minimizes polarization. As an example of such an adjustment, see U.S. Pat. No. 4,343,312, incorporated herein by reference. In a currently preferred embodiment, as discussed below, a fixed resistor is used for fixing the pre-stim duration, while the post-stim duration is adjusted until the polarization after delivery of the entire pulse is of a polarity opposite to the stimulus, e.g., positive, and is within predetermined limits. The polarization is sensed by the sense amplifier, e.g., by being positive level triggered at a predetermined sensitivity. In a preferred embodiment, the post-stim duration, or interval, is first set to a value such as 6 ms, which ensures a resulting positive polarization (for a negative stimulus). After this, the post-stim duration is decreased in steps until the polarization after the pulse is found to be within a range of levels, e.g., plus 0.5 mV to 1.0 mV. This represents a minimal polarization level, which enables reliable evoked response detection by simply looking for a negative-going signal following the blanking interval. Note that as used herein, the terms minimize and minimization refer to reducing polarization to a desired level. At about 0.5 to 1.0 mV, the polarization is not sufficient to mask the cardiac signals which the pacemaker must detect; and also, this level means that a negative-going signal within a short window after the blanking period is more than noise, and can reliably be interpreted as the evoked response.

Figure 2B:
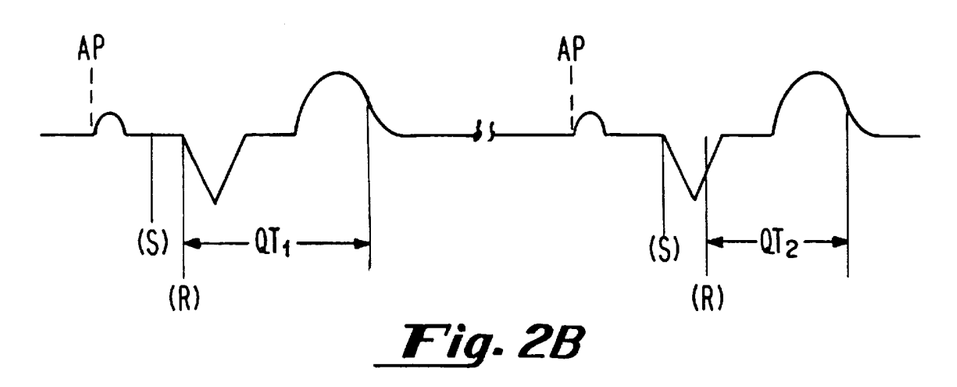
FIG. 2B is a timing diagram indicating delivery of pulse pairs to a patient's ventricle, each pair comprising a first search pulse and a second regular pace pulse, illustrating how ventricular capture by the search pulse can be detected.
Figure 2C:
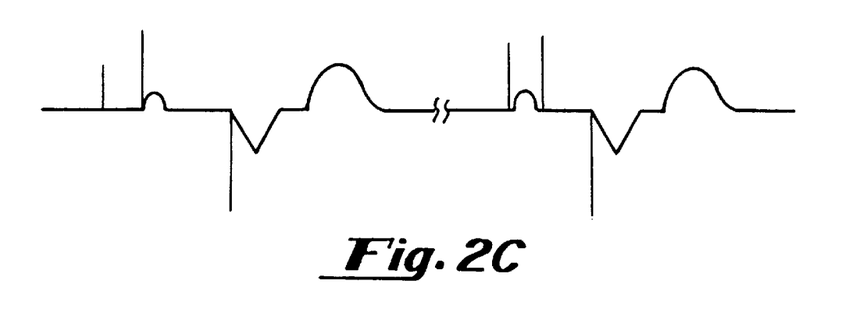
FIG. 2C is a timing diagram showing capture detection by delivery of similar pulse pairs to a patient's atrium.

Referring to FIG. 2B, there is shown a timing diagram illustrating delivery of a pair of pulses in accordance with this invention, e.g., a first search pulse and a second regular pacing pulse. FIG. 2B shows a threshold test being performed for ventricular pacing. Following a first atrial pulse and resulting atrial evoked response and an AV delay, a search pulse (S) and regular pulse (R) are delivered. As indicated, the regular pulse captures the ventricle, resulting in a QRS complex and T-wave. The time between the delivery of the regular pace pulse and the T-wave is indicated as $Q-T_1$. At a later time, after the search pulse output level has been raised above threshold and stabilized, it is seen that the search pulse captures the ventricle, not the regular pulse, and that $QT_2$ is decreased relative to $QT_1$. FIG. 2C is a similar timing diagram, applied to the threshold test for atrial pace pulses, again showing a first pair where the search pulse does not capture the atrium, and second pair where the search pulse does capture the atrium. It is to be noted that FIGS. 2B and 2C are illustrative of the timing involved, and that the intracardiac signals as seen by an implanted pacemaker may differ slightly in ways that are not relevant to the explanation of this invention.

Figure 3A:
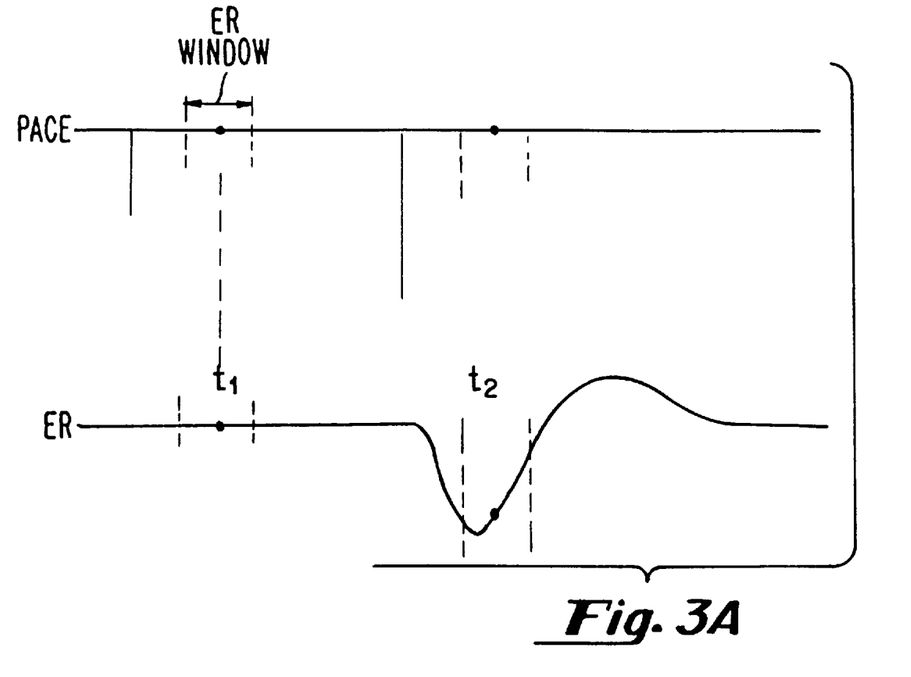
FIG. 3A comprises a pair of timing diagrams which illustrate the use of a sensing window, where the regular pulse captures the heart.
Figure 3B:
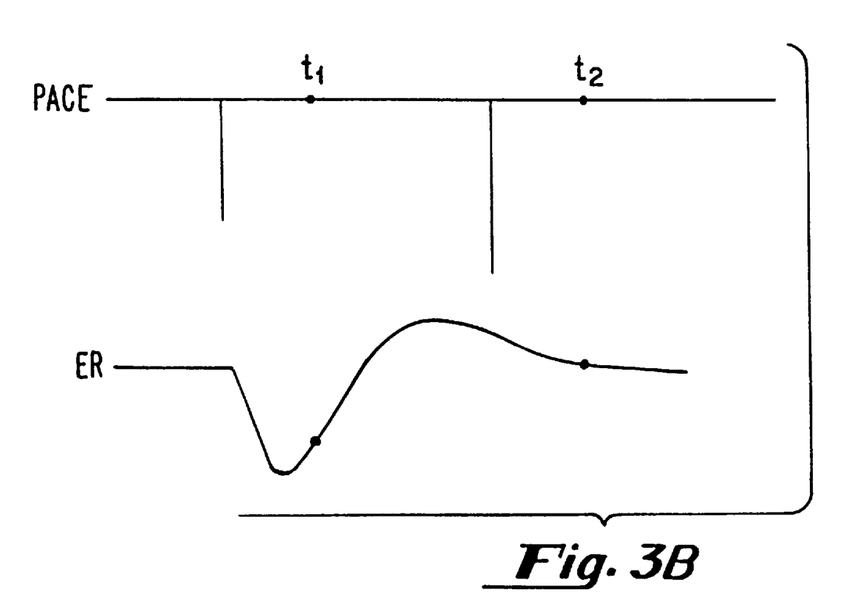
FIG. 3B is a similar pair of timing diagrams illustrating use of a sensing window, where the search pulse of the pulse pair captures the heart.

Referring to FIG. 3A, there is illustrated the technique of providing an evoked response window following each delivered pace pulse, for determining whether there has been an evoked response. As seen in the upper timing diagram of FIG. 3A, a first search pulse is delivered, and an evoked response window is timed out centered about a time $t_1$ following the search pulse. As seen in the lower timing diagram, the search pulse does not evoke a response, and there is no detected evoked response during the search window. When the regular pace pulse is delivered, a window is timed out centered about time $t_2$ following the regular pulse, and during this regular window the sense amplifier sees the evoked response. Referring to FIG. 3B, the same pulse pair is shown, but in this instance the evoked response is seen during the search window centered around time $t_1$. This window technique enhances specific detection of the evoked response, i.e., for determining whether it was the search pulse or the regular pulse that evoked the response.

Figure 4:
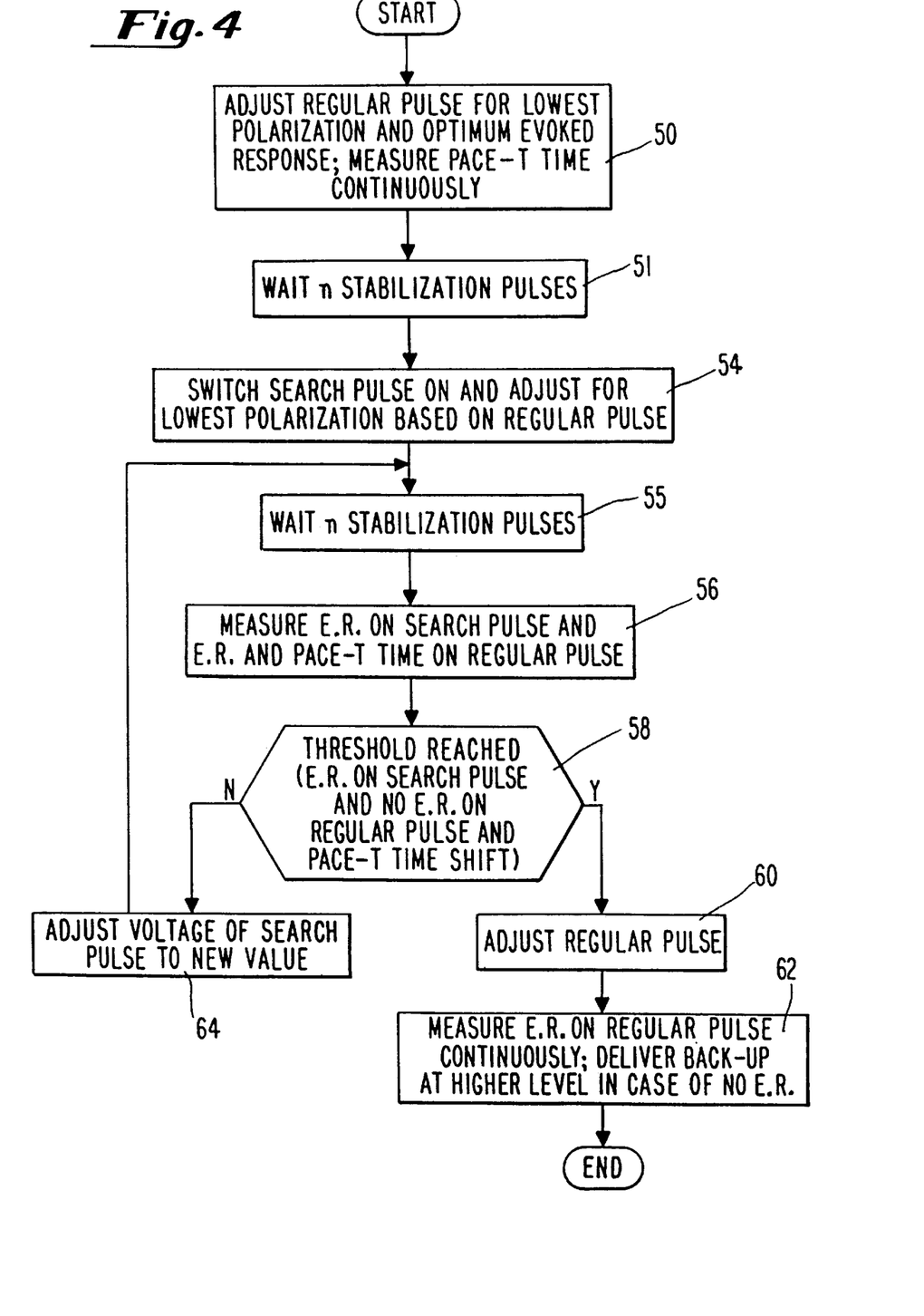
FIG. 4 is a flow diagram showing the primary steps of a threshold detection routine in accordance with this invention.

Referring now to FIG. 4, there is shown a flow diagram of the primary steps in carrying out the capture detection and threshold search feature of this invention. The algorithm starts by adjustment of the regular pulse for lowest polarization and optimum evoked response, as indicated at 50. Such adjustment may be made as discussed above, and as discussed further below in connection with FIG. 5. Following this, the pacemaker measures the pace-T time, or "QT" interval, continuously. As indicated at 51, the test waits for a predetermined number n of delivered pulses, to allow stabilization of the polarization pattern. The stabilization can vary, and the waiting period is a matter of design choice. For example, n can vary between 0 and 20. However, it is an important feature to make sure that there is a stabilization period. Following this, as indicated at 54, the pacemaker begins to deliver pulse pairs, switching on a second, search pulse, and adjusting the search pulse for lowest polarization. Here, the adjustment of the search pulse may be made based on the adjustment of the triphasic pulse components made for the regular pulse, i.e., the same relative heights and durations of the pulse portions may be utilized. Following this, as indicated at 55, the pacemaker again waits a predetermined time, e.g., 10 stabilization pulses. Only after both the regular pulse and the search pulse have been stabilized, is measurement of the evoked response undertaken. Optionally, at the end of the stabilization interval, the polarization immediately after delivery of a pulse can be checked to see if it remains within the predetermined limits. If not, the post-stim duration can be further adjusted.

At 56, evoked response is sensed following the search pulse and the regular pulse, and the pace-T time relative to the regular pulse is measured. Following this, at 58, it is determined whether the threshold has been reached, i.e., whether an evoked response is sensed by the sense amplifier following the search pulse. Optionally, as indicated, threshold can be verified by examining the pace-T time interval, and determining whether it has shifted, as discussed above. Of course, at the beginning of the test, it is anticipated that the search pulse output level has been set below threshold, such that it does not capture. When threshold has not been reached by the search pulse, the routine exits to block 64, and adjusts the search pulse output upwardly to a new value. The routine then goes back to block 55, and again waits for 10 stabilization pulses before going to the steps of capture detection and threshold determination. Thus, the routine may cycle a number of times until the search pulse has incremented above threshold. Importantly, each time the search pulse output is incremented, a new stabilization interval is invoked, in order to minimize polarization within the desired limits, and to enable reliable capture detection.

It is to be understood that block 58 can be modified. For example, the pacemaker can look for 1, 2, 3 . . . or n delivered pulse pairs where the search pulse is determined to capture the heart, where n can be 2 or greater to ensure that threshold has been reached.

After threshold has been reached by the search pulse, the routine branches to step 60 and, if desired, adjusts the regular pulse accordingly, i.e., at a safety value above threshold. Following this, as indicated at 62, the pacemaker paces continuously with the regular pulse, measuring evoked response on each delivered pulse. In the case of no evoked response, a back-up pulse can be delivered to avoid skipping a heartbeat. Note that adjustment at step 60 may not be required, particularly if the change would be very little. Also, the pacemaker may be programmed to periodically obtain a threshold reading only for diagnostic purposes, e.g., to record threshold trend, construct a threshold histogram, etc. Also, although not shown, the maximum value of the evoked response can be measured, and the sense amplifier sensitivity adjusted, e.g., to a value of about one-half the maximum evoked response amplitude.

It is to be understood that the capture detection and search features of this invention can be employed during clinical follow-up, in which case it is initiated by an external programmer. In this setting, the measured values will be communicated to the programmer, and the physician can re-program pace pulse output level as indicated. Alternately, the feature can be performed automatically, e.g., after a programmable period such as 12 or 24 hours. The threshold value that has been found is stored by the pacemaker, and upon next initiating a threshold test, the search pulse is set at a predetermined level relative to the last determined threshold, to optimize the test procedure. For example, if the latest measured threshold value was 0.5V, the threshold test can start automatically with a search pulse at 0.4V and a regular pulse at the regular output (for example 2.5V). If 0.4V does not result in capture, the next search pulse amplitude will be 0.6V (right above the previous threshold value). This way, the threshold procedure will be performed in a minimal amount of time.

In the practice of this invention, the capture detection feature can be used without a threshold detection test. Thus, the pacemaker may be enabled to automatically adjust the stimulus pulse parameters, wait out a stabilization period, and proceed with capture detection. In the event that an evoked response is not sensed at any time, a back-up stimulus is delivered, and the stimulus output is adjusted upward by a predetermined increment.

Figure 5:
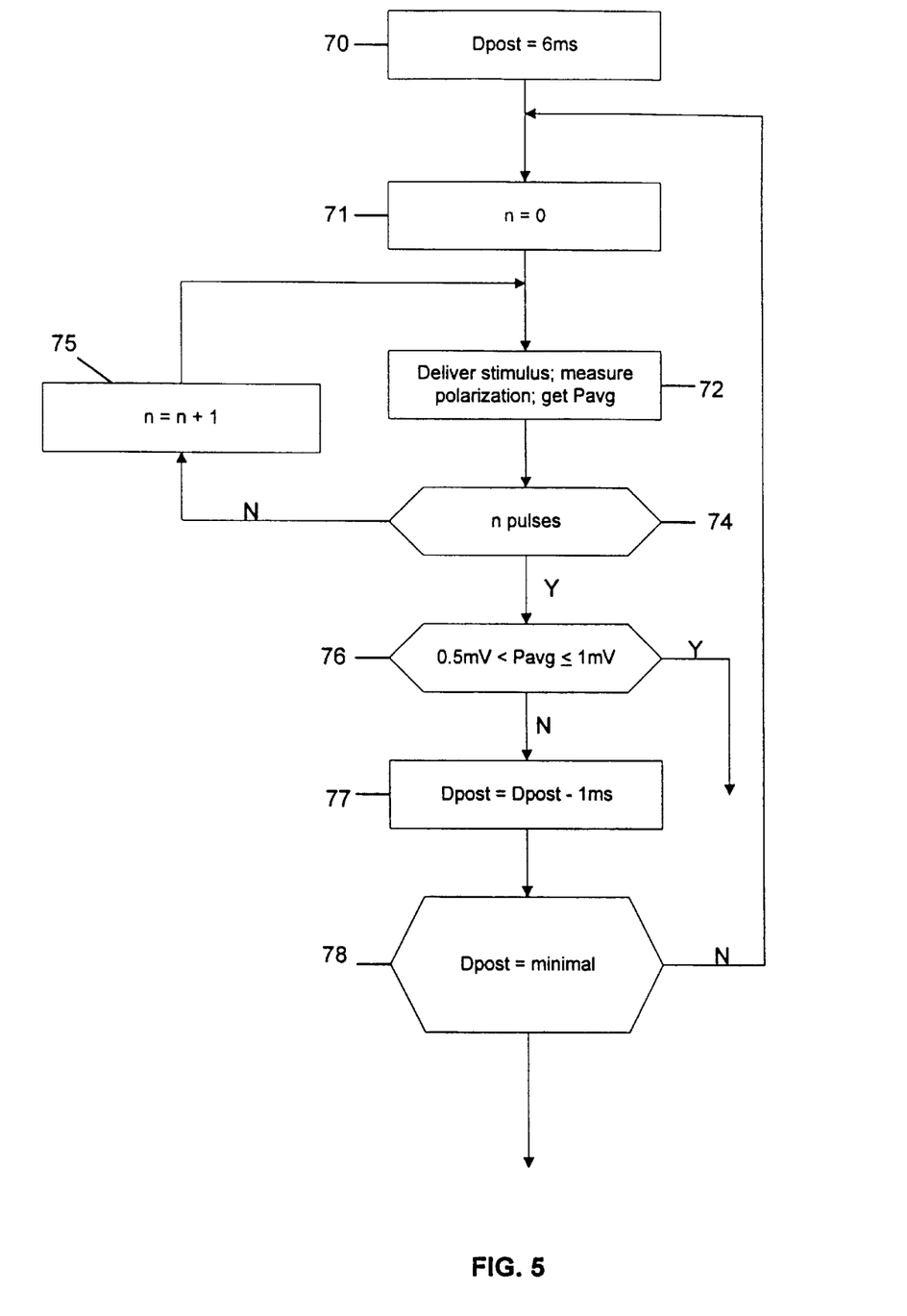
FIG. 5 is a flow diagram of a routine for adjusting pace pulses for minimization of polarization, in accordance with this invention.

Referring now to FIG. 5, there is shown a flow diagram of the main steps taken in a preferred embodiment for minimizing polarization to the desired range. At 70, the duration of the post-stim pulse portion, Dpost as seen in FIG. 2A, is initially set to a predetermined value, e.g., 6 ms. At 71, a variable n is set to zero. At 72, the pacemaker delivers a stimulus pulse, which has a post-stim duration as set, e.g., initially 6 ms. The polarization following a normal blanking period is sensed by the sense amplifier and is measured. This is done repeatedly, and a value of the average polarization level for the series of n pulses, Pavg, is calculated. Then, at 74, it is determined whether the series of n pulses has been delivered; if not, the value of n is incremented by one, as seen at 75, and the routine loops back to block 72 to deliver the next pulse and update Pavg. When n pulses have been delivered, the routine proceeds to block 76 and determines whether Pavg is within the predetermined limits, e.g., greater than 0.5 mv and less than 1.0 mv. If yes, the routine exits, since the present value of post-stim duration corresponds to the desired polarization level. If not, then the routine proceeds to block 77 and decrements the post-stim duration by, e.g., 1 ms. At 78, it is determined whether Dpost is equal to a predetermined minimal value, which is a function of lead impedance. If not, the routine loops back to 71 and delivers another set of pace pulses with the adjusted value of Dpost, again determining whether the polarization is within the set limits. Whenever the desired polarization level is found, the routine exits. If the minimum value of Dpost is reached, the routine exits with Dpost set equal to such minimal value.

In practice, the routine of FIG. 5 need not be run very often. It can be run after pacemaker implant, when chronic electrode fixation is achieved, and thereafter the polarization need not be adjusted, except for threshold testing. Optionally, the polarization routine can be run periodically, or on command from an external programmer.

Figure 6:
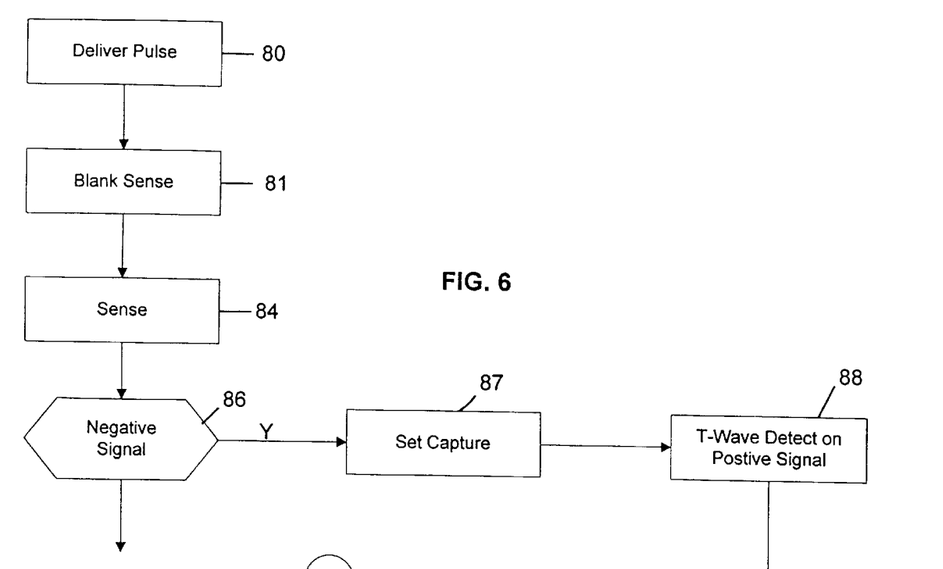
FIG. 6 is a flow diagram of a the steps taken in accordance with an embodiment of this invention for detecting evoked responses and T-waves after polarization minimization.

Referring now to FIG. 6, there is illustrated a flow diagram of the primary steps taken in accordance with the system and method of this invention for detecting evoked ventricular responses (R waves) and repolarization signals (T-waves). At 80, a pulse is delivered, either triphasic as illustrated in FIG. 2A, or biphasic, the post-stim duration being adjusted to result in minimal polarization as discussed above. At 81, the sense amplifier for sensing signals in the ventricle is blanked for a short duration, in a known manner. Then, as shown at 84, the sense amplifier circuit is enabled. This step may include enabling the amplifier for a window of time following the blanking interval, in a known manner. If a negative signal is determined, as seen at 86, then at 87 the pacemaker interprets that capture has occurred. At 88, the sense amplifier is enabled, again preferably for a window of time corresponding to the expected occurrence of the T-wave. T-wave sensing occurs in a known manner.

Figure 7:
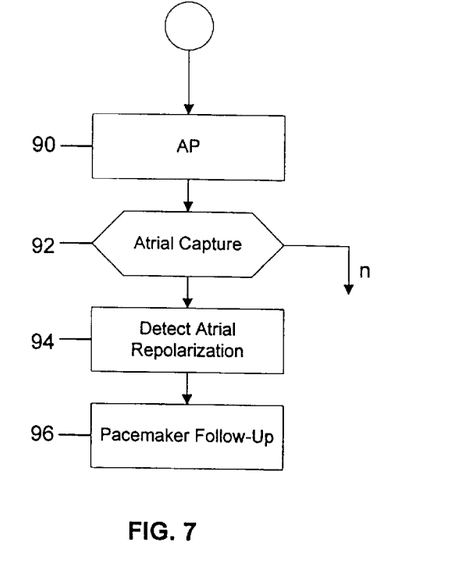
FIG. 7 is a simplified flow diagram of the steps of detecting atrial capture by a delivered atrial pace pulse; detecting atrial repolarization; and utilization of the atrial repolarization signal for pacemaker follow-up.

Referring now to FIG. 7, there is shown a flow diagram for determining evoked response to a delivered atrial pulse, as well as for detecting atrial repolarization. At 90, a triphasic or biphasic stimulus pulse is delivered, with adjusted post-stim duration in accordance with the above discussion. At 92, atrial capture is determined, again as described above for determining an evoked response. Following this, the repolarization signal is detected in the same manner as discussed in connection with FIG. 6 for the ventricular case. Following this, at 96 the pacemaker follows-up to use the information about the repolarization signal, in accordance with the manner in which the pacemaker has been programmed. For example, for an AAIR pacemaker, the stimulus-repolarization interval is determined, for control of atrial pacing rate in the same manner as is done for a VVIR pacemaker which uses Q-T interval as the rate control parameter. Likewise, the timing of the atrial repolarization can be used for treating atrial arrhythmias or for inducing such; atrial repolarization can be monitored to determine response to drug treatment; etc.

The polarization optimization routine of this invention can be employed at a frequency programmed at implant, or later. As is known, polarization varies in time, and is a function of the lead. As used herein, the polarization level is the level of the polarization detected by the sense amplifier, across the output electrodes. Thus, when it is stated that polarization is detected at the lead electrode, this means between the tip electrode and the pacemaker can for a unipolar system, or between the tip electrode and ring electrode for a bipolar system. The frequency of carrying out the polarization optimization routine can be once daily following implantation, and adjusted to longer intervals when chronic lead conditions are reached.

What is claimed is:

1. A pacemaker system for delivering pace pulses to a patient's heart, comprising:

a controllable pulse generator for delivering pace pulses comprising a stimulus pulse portion of a first polarity and a post-stim portion of a second polarity;

control means for controlling the duration of said post-stim pace pulses;

a lead for delivering said pace pulses, said lead having at least one electrode at about its distal end;

sensing means for sensing signals at said electrode, and polarization level means for determining the level of polarization signals sensed at said electrode; and said control means having program means for programming said post-stim pace pulse duration to a value at which the level of a said polarization signal following a delivered pace pulse is within predetermined limits, wherein said program means comprises means for adjusting said post-stim portion to different values in a predetermined sequence until said polarization signals are determined to be within said limits.

2. The system as described in claim 1, comprising cardiac signal means for recognizing cardiac signals sensed at said electrode, and evoked response means for determining when there has been an evoked response following a said delivered pace pulse.

3. The system as described in claim 2, comprising timing means for enabling said evoked response means after a first time duration following a delivered pace pulse.

4. The system as described in claim 3, wherein said program means has positive means for programming said post-stim duration to a value at which the level of polarization signals following delivered pace pulses is a positive value within said limits, and wherein said evoked response means comprises means for detecting a negative-going signal.

5. The system as described in claim 4, wherein said pulse generator means comprises triphasic means for generating and delivering pace pulses comprising a pre-stim positive portion, a negative stimulus portion, and a post-stim positive portion.

6. The system as described in claim 1, comprising threshold determining means for determining patient threshold to delivered pace pulses having said programmed post-stim pulse duration.

7. The system as described in claim 6, wherein said threshold means comprises means for determining that said post-stim polarization is within said limits following a predetermined number of consecutive said pacing pulses delivered at a predetermined stimulus level.

8. The system as described in claim 1, wherein said program means comprises means for setting said polarization signal limits at about 0.5 mV to 1.0 mV.

9. A method of generating stimulus pulses for delivery to an electrode positioned in proximity to a patient's heart, each said stimulus pulse having a stimulus portion of a first polarity and a post-stim portion of an opposite polarity, comprising:

setting the magnitude and duration of said stimulus portion;

setting the magnitude and duration of said post-stim portion;

adjusting said post-stim duration and delivering stimulus pulses and determining the polarization level at said electrode following delivery of stimulus pulses, and continuing said adjusting and delivering and determining until the post-stim portion is optimally adjusted so that said polarization level is within predetermined limits; and generating stimulus pulses having a said stimulus portion and a said optimally adjusted post-stim portion, comprising generating said stimulus portion with a negative polarity and said post-stim portion with a positive polarity, and initially setting said post-stim duration to a value selected so that the polarization following delivery of a stimulus pulse is positive.

10. A method of generating stimulus pulses for delivery to an electrode positioned in proximity to a patient's heart, each said stimulus pulse having a stimulus portion of a first polarity and a post-stim portion of an opposite polarity, comprising:

setting the magnitude and duration of said stimulus portion;

setting the magnitude and duration of said post-stim portion;

adjusting said post-stim duration and delivering stimulus pulses and determining the polarization level at said electrode following delivery of stimulus pules, and continuing said adjusting and delivering and determining until the post-stim portion is optimally adjusted so that said polarization level is within predetermined limits; and generating stimulus pules having a said stimulus portion and a said optimally adjusted post-stim portion, comprising generating said stimulus portion with a negative polarity and said post-stim portion with a positive polarity, and initially setting said post-stim duration to a value selected so that the polarization following delivery of a stimulus pulse is positive, comprising determining when the polarization following delivery of a said stimulus pulse is positive and within a range of about 0.5 to 1.0 mV, determining the post-stim duration which results in polarization within said range, and thereafter generating said stimulus pulses with said determined post-stim duration.

11. A method of generating stimulus pulses for delivery to an electrode positioned in proximity to a patient's heart, each said stimulus pulse having a stimulus portion of a first polarity and a post-stim portion of an opposite polarity, comprising:

setting the magnitude and duration of said stimulus portion;

setting the magnitude and duration of said post-stim portion;

adjusting said post-stim duration and delivering stimulus pulses and determining the polarization level at said electrode following delivery of stimulus pulses, and continuing said adjusting and delivering and determining until the post-stim portion is optimally adjusted so that said polarization level is within predetermined limits; and generating stimulus pulses having a said stimulus portion and a said optimally adjusted post-stim portion, comprising generating said stimulus portion with a negative polarity and said post-slim portion with a positive polarity, and initially setting said post-stim duration to a value selected so that the polarization following delivery of a stimulus pulse is positive, comprising determining when the polarization following delivery of a said stimulus pulse is positive and within a range of about 0.5 to 1.0 mV, determining the post-stim duration which results in polarization within said range, and thereafter generating said stimulus pulses with said determined post-stim duration, further comprising detecting an evoked response following delivery of said stimulus pulse with said determined post-stim duration by sensing a negative signal.

12. A system for optimizing polarization following delivery of pacing pulses to a patient, said pacing pulses being triphasic and having a positive post-stim portion, comprising:

means for generating said triphasic pulses;

means for delivering said triphasic pulses to a pair of electrodes being positioned so that said pulses stimulate said patient's heart;

means for sensing the polarization level at said electrodes following a delivered pacing pulse;

means for adjusting said post-stim portion to obtain a following polarization within predetermined limits; and polarization optimization means for enabling said means for sensing and said means for adjusting, and program means for programming said polarization optimization means to operate at predetermined times, said program means is programmed to operate said polarization optimization means at a predetermined frequency, wherein said program means has means for lengthening the interval between operations after said system has been implanted for at least a predetermined time.

13. The system as described in claim 12, comprising means for determining when a negative signal occurs within a predetermined time window following a delivered pacing pulse, thereby determining when there has been an evoked response.

* * * * *